US011375824B2

(12) United States Patent
Bussert (10) Patent No.: US 11,375,824 B2
(45) Date of Patent: Jul. 5, 2022

(54) THERAPEUTIC SEAT CUSHION EQUIPPED FOR PRESSURE MONITORING AND INFLATION SYSTEM FOR SAME

(71) Applicant: BUSSERT MEDICAL, INC, Nashville, IN (US)

(72) Inventor: Jessica Bussert, Nashville, IN (US)

(73) Assignee: BUSSERT MEDICAL, INC., Nashville, IN (US)

( * ) Notice: Subject to any disclaimer, the term of this patent is extended or adjusted under 35 U.S.C. 154(b) by 142 days.

(21) Appl. No.: 16/982,806

(22) PCT Filed: Mar. 22, 2019

(86) PCT No.: PCT/US2019/023630
§ 371 (c)(1),
(2) Date: Sep. 21, 2020

(87) PCT Pub. No.: WO2019/183502
PCT Pub. Date: Sep. 26, 2019

(65) Prior Publication Data
US 2021/0059426 A1 Mar. 4, 2021

Related U.S. Application Data

(60) Provisional application No. 62/646,592, filed on Mar. 22, 2018, provisional application No. 62/736,672, filed on Sep. 26, 2018.

(51) Int. Cl.
*A47C 27/08* (2006.01)
*A47C 7/14* (2006.01)
*A47C 27/10* (2006.01)

(52) U.S. Cl.
CPC ............ *A47C 27/083* (2013.01); *A47C 7/142* (2018.08); *A47C 7/144* (2018.08); *A47C 27/082* (2013.01); *A47C 27/10* (2013.01)

(58) Field of Classification Search
None
See application file for complete search history.

(56) References Cited

U.S. PATENT DOCUMENTS 3,527,207 A 9/1970 Gottfried
3,867,732 A 2/1975 Morrell
(Continued)

FOREIGN PATENT DOCUMENTS

CN 103974681 B 12/2017
WO 100132 A2 4/2001

OTHER PUBLICATIONS

EPO, Supplementary European Search Report, Nov. 25, 2021, 161 pages, Munich Germany.

*Primary Examiner* — David E Allred
(74) *Attorney, Agent, or Firm* — Brannon Sowers & Cracraft PC (57) ABSTRACT

A seat cushion includes a plurality of inflatable cells, a pumping mechanism, and a manifold or valve system fluidly between the pumping mechanism and the inflatable cells. The manifold or the valve system, which may include a clutch and a motor, connect the pumping mechanism with the inflatable cells such that a plurality of zones are created. A valve assembly can include a plurality of valves and is adjustable among at least three valve configurations to vary fluid connections to the inflatable cells to produce rearwardly advancing waves. The pumping action produced by the inflation and deflation of the inflatable cells assists in pumping blood in a user's legs back toward the heart.

18 Claims, 5 Drawing Sheets

(56) References Cited

U.S. PATENT DOCUMENTS

| | | | |
|---|---|---|---|
| 3,935,690 | A | 2/1976 | Lea et al. |
| 5,267,364 | A | 12/1993 | Wolk |
| 5,584,085 | A | 12/1996 | Banko |
| 6,014,784 | A | 1/2000 | Taylor et al. |
| 6,058,537 | A | 5/2000 | Larson |
| 7,587,776 | B2 | 9/2009 | Poulos |
| 2003/0159219 | A1 | 8/2003 | Harrison et al. |
| 2006/0004518 | A1* | 1/2006 | Sleboda ............ B60R 21/01516 180/272 |
| 2006/0075559 | A1* | 4/2006 | Skinner .............. A61G 7/05769 5/655.3 |
| 2012/0317720 | A1 | 12/2012 | Ciang et al. |
| 2014/0223665 | A1 | 8/2014 | Chapin |
| 2014/0298588 | A1 | 10/2014 | Riley et al. |
| 2015/0238022 | A1 | 8/2015 | Chapin |
| 2016/0317370 | A1 | 11/2016 | Evans |
| 2016/0332026 | A1* | 11/2016 | Hiroura .................. G16H 20/40 |
| 2017/0103524 | A1* | 4/2017 | Franz ........................ G06T 7/73 |
| 2019/0117124 | A1* | 4/2019 | Hsu ...................... A61B 5/6892 |
| 2019/0183255 | A1* | 6/2019 | Louks .................. A47C 27/083 |
| 2019/0201271 | A1* | 7/2019 | Grey .................... A47C 31/001 |

* cited by examiner

THERAPEUTIC SEAT CUSHION EQUIPPED FOR PRESSURE MONITORING AND INFLATION SYSTEM FOR SAME

CROSS-REFERENCE

This patent application claims priority to U.S. provisional patent application Ser. No. 62/736,672, filed on Sep. 26, 2018, and provisional patent application Ser. No. 62/646,592, filed on Mar. 22, 2018.

TECHNICAL FIELD

The present disclosure relates generally to a therapeutic seat cushion, and more particularly to a therapeutic seat cushion structured and controlled to produce rearwardly advancing waves, for enhanced comfort and massaging action or to assist the body's natural blood pumping action.

BACKGROUND

U.S. Pat. No. 6,782,573 to Odderson is directed to a Body Supporting, Serial Inflating Seat. In Odderson, inflatable bladders are inflated one after another in series to purportedly help circulate blood in the legs of a user. While Odderson might have certain applications, there is ample room for alternative strategies and improvements in this field.

SUMMARY OF THE INVENTION

In one aspect, a therapeutic cushion system includes a pumping mechanism, and a seat cushion having inflatable cells arranged in series between a front seat cushion edge and a rear seat cushion edge. The seat cushion further includes a manifold having at least one inflation inlet in fluid communication with the pumping mechanism, and at least one deflation outlet. The therapeutic cushion system further includes a valve assembly adjustable among at least three different valve configurations, and fluidly connecting some of the inflatable cells to the at least one inflation inlet and some of the inflatable cells to the at least one deflation outlet in each of the different valve configurations. An electronic control unit is structured to adjust the valve assembly among the at least three different valve configurations such that inflation/deflation of the inflatable cells produces a plurality of rearwardly advancing pumping waves.

In another respect, a therapeutic cushion system includes a pumping mechanism, a seat cushion including inflatable cells arranged in series between a front seat cushion edge and a rear seat cushion edge, and an electronic control unit. The seat cushion further includes a valve system having a motor coupled with a valve assembly having a valve member movably positioned within a valve case, at least one pump inlet in fluid communication with the pumping mechanism, and at least one outgas bore. The valve assembly is adjustable among at least three different inflation configurations, and fluidly connects some of the inflatable cells to the at least one pump inlet and some of the inflatable cells to the at least one outgas bore in each of the different valve configurations. The electronic control unity is structured to adjust the valve assembly among the at least three different valve configurations such that inflation/deflation of the inflatable cells produces a plurality of advancing pumping waves.

DETAILED DESCRIPTION

Figure 1:
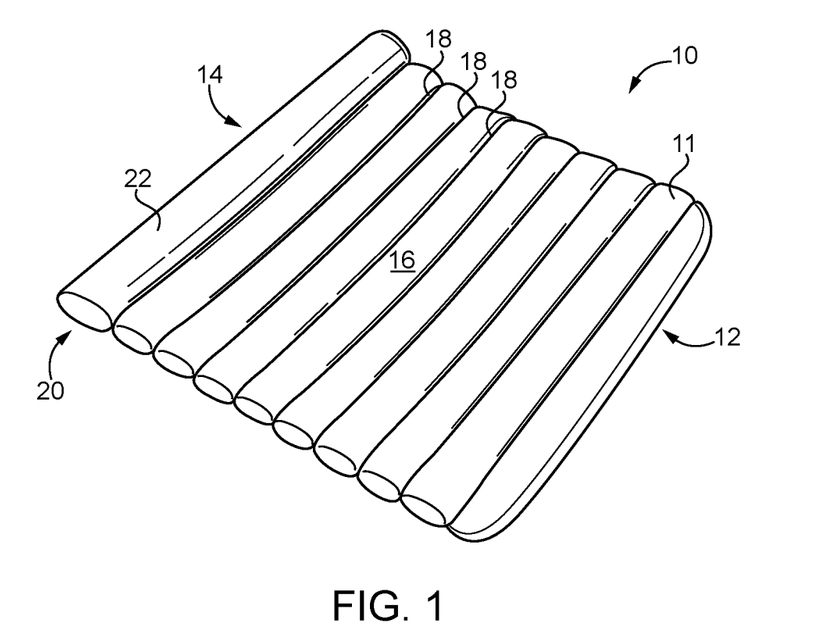
FIG. 1 is a perspective view of a cushion system according to one embodiment in a use configuration.

Referring to FIG. 1 there is shown a therapeutic seat cushion/seat cushion system 10 (hereinafter "cushion 10") according to one embodiment. Cushion 10 is shown as it might appear in a use configuration to be sat upon by a user. Cushion 10 includes a cover 11, formed for example from a fabric, having a front or forward seat cushion edge 12 and a back or rear seat cushion edge 14. A rear receptacle 22 adjacent to rear edge 14 has a cavity formed therein that contains various electronics and other components, as further discussed herein. Creases or grooves 18 formed in cover 11 extend widthwise and are generally, structured to fit about inflatable cells (not visible in FIG. 1) that are within cover 11, and are interspersed among the inflatable cells. Grooves 18 form fold lines along which cover 11 is folded when rolled-up for storage and/or packaged for retail. In a practical implementation strategy, inflatable cells in cushion 10 may be arranged in a right side or right-hand series and a left side or left hand series, with the inflatable cells arranged in series between front edge 12 and rear edge 14. In other instances, a single series of inflatable cells may be provided, approximately as shown. Also visible in FIG. 1 is a plug or port 20, such as a Universal Services Bus (USB) port, for connecting cushion 10 to a power supply and/or data communication link. It will be appreciated that cushion 10 may be used in a passenger vehicle or institutional setting, and the prevalence of USB ports for electric power in modern passenger vehicles makes USB connectivity an advantageous feature. A conventional AC connector plug could additionally or alternatively be used, or some other electrical power supply connector or interface. As will be further apparent from the following description, cushion 10 may be equipped with internal components and computer control hardware and software to enable the inflatable cells to be inflated and deflated in a manner that produces rearwardly advancing pumping waves to assist in pumping blood from a user's legs back toward the heart and lungs. The manner of inflation and deflation can be customizable on the basis of user preference, or to carry out prescribed therapeutic treatments for instance.

Figure 2:
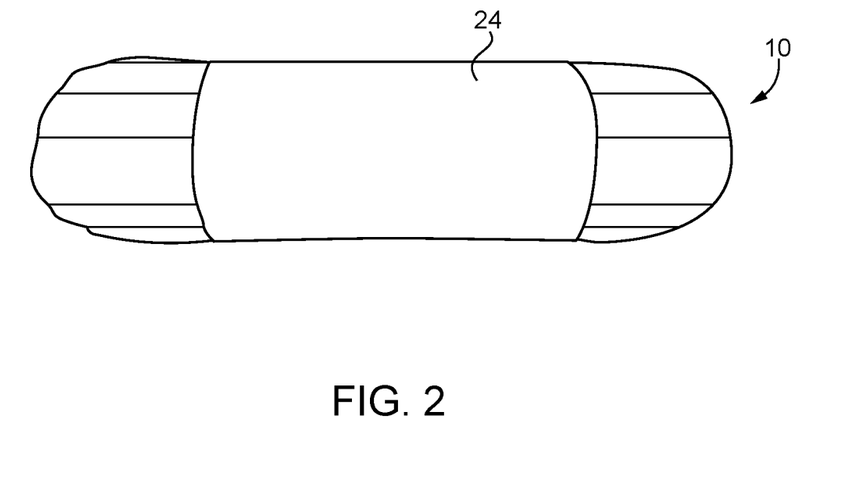
FIG. 2 is a diagrammatic view of a packaged cushion system in a rolled-up configuration.

Referring to FIG. 2 there is shown cushion 10 as it might appear in a rolled-up configuration and retained within the rolled-up configuration in a package 24 such as a packaging tube, wrap, or the like. The inflatable cells may be arranged in series as noted above, extending widthwise across cushion 10. Together with creases/grooves 18 the arrangement of inflatable cells makes cushion 10 well suited to rolling up and packaging when deflated such as for storage or commercial display and retail sale.

Figure 3:
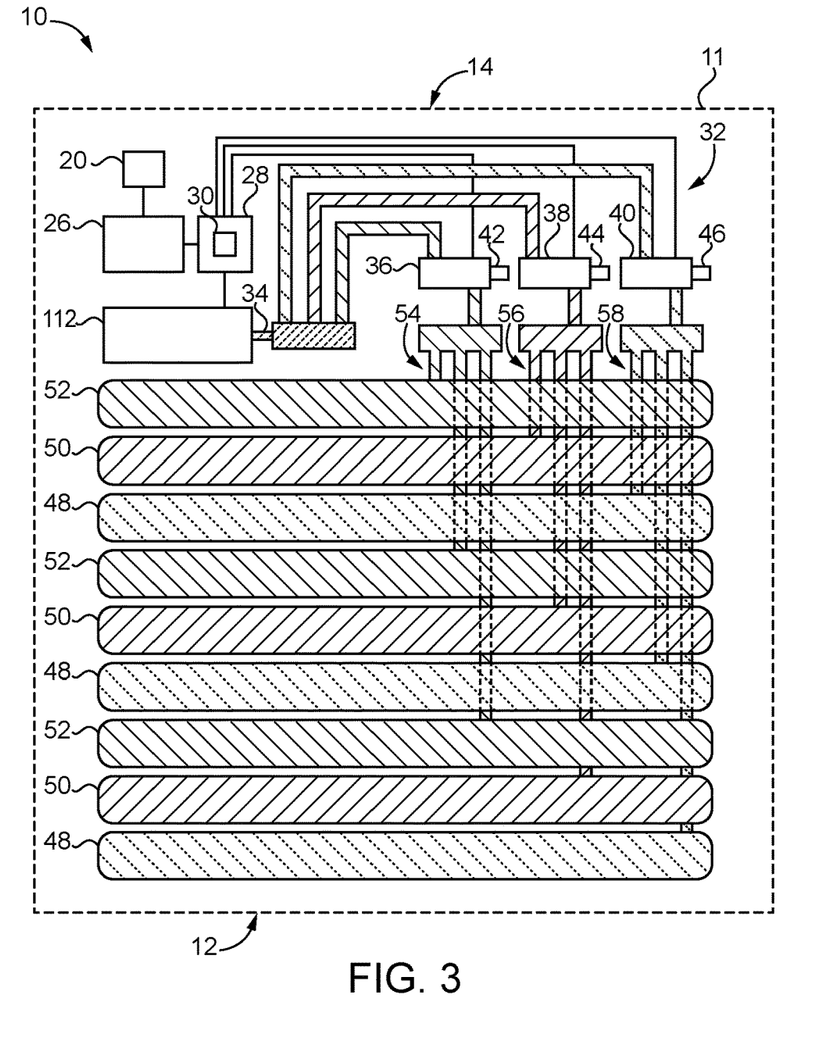
FIG. 3 is a schematic illustration of a cushion system, according to one embodiment.

Turning now to FIG. 3, there is shown a schematic view of cushion 10 illustrating internal components. It can be seen that a battery 26 is connected with plug 20 for charging. Control circuitry 28, including an electronic control unit 30 such as a microprocessor or microcontroller, is coupled with battery 26 and also with a pumping mechanism 112. Pumping mechanism 112 can include an air pump in one embodiment, although the present disclosure is not thereby limited and other inflation fluids, as well as various pump designs or other sources of fluids for fluid flow could be used. A source of pressurized fluid for actuating cushion 10 could be external, for instance. In such an embodiment fluid inlet 34 could be positioned externally of cushion 10. At least one fluid inlet 34 connects pumping mechanism 112 (hereinafter "pump 112") with a manifold or manifold system 32. An electrically actuated valve assembly is positioned fluidly between fluid inlet 34 and a plurality of inflatable cells 48, 50, and 52, the arrangement of which is further described herein. The electrically actuated valve assembly can include a plurality of valve mechanisms 36, 38, and 40, which can include slide-type hydraulic valves such as spool valves, or poppet valves, for example, each of which is equipped with an electrical actuator that varies energy state responsive to a control signal from electronic control unit 30. The valve assembly can be adjustable among a plurality of different valve configurations, including at least three valve configurations, to vary fluid connections between inflation inlet 34 and inflatable cells 48, 50, and 52, and also between at least one deflation outlet 42, 44, and 46 and inflatable cells 48, 50, and 52, the significance of which is further discussed below.

For convenience of distinguishing between different cells, it will be noted inflatable cells 48 are designated as colored red (with a first shading pattern in the drawings), inflatable cells 50 are designated as colored green (with a second shading pattern in the drawings), and inflatable cells 52 are designated as colored blue (with a third shading pattern in the drawings) herein. Fluid conduits 54 extend between valve mechanism 36 and the blue inflatable cells 52. Fluid conduits 56 extend between valve mechanism 38 and green inflatable cells 50, whereas fluid conduits 58 extend between valve mechanism 40 and red inflatable cells 48. In one implementation all of inflatable cells 48, 50, and 52 as well as conduits 54, 56, and 58 can be formed by radiofrequency (RF) welding together two sheets of plastic or other suitable polymeric material to selectively create joints or seams. It will be appreciated that other strategies for forming inflatable cells and suitable plumbing are possible.

Figure 4:
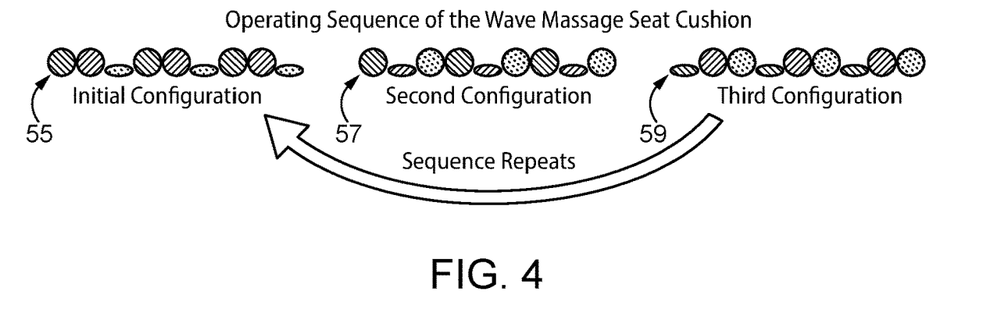
FIG. 4 is a concept diagram illustrating an operating sequence of a cushion system, according to one embodiment.

As noted above the valve assembly can provide selective connections at any one time of some of the inflatable cells to inflation inlet 34 and some of the inflatable cells to deflation outlet(s) 42, 44, and 46. FIG. 4 sets forth an example inflation/deflation sequence that includes three or more inflation configurations of inflatable cells 48, 50, 52. The number of inflation configurations may be based on the number of inflatable cell groups within cushion 10. For example, cushion 10 of the present embodiment includes three groups of inflatable cells that can be inflated or deflated to form three distinct inflation configurations: an initial configuration 55, a second configuration 57, and a third configuration 59. It will be appreciated, however, that there may not always be a 1:1 correlation between the number of inflatable cell groups and the number of inflation configurations. Generally, as the number of inflatable cell groups increases, so does the number of possible inflation configurations. By selectively connecting, for instance, red inflatable cells 48 to deflation outlet 46 while green inflatable cells 50 and blue inflatable cells 52 are connected to inflation inlet 34 (i.e., initial configuration 55), then connecting green inflatable cells 50 to deflation outlet 44 while blue inflatable cells 52 and red inflatable cells 48 are connected to inflation inlet 34 (i.e., second configuration 57), and then connecting blue inflatable cells 52 to deflation outlet 42 while red inflatable cells 48 and green inflatable cells 50 are connected to inflation inlet 34 (i.e., third configuration 59), rearwardly advancing pumping waves can be produced. Another way to understand the principle is that some of the inflatable cells are connected to incoming inflation fluid (typically air) while others are connected to exhaust/deflation, and then the arrangement/connections are varied to enable the wave(s) to push or propagate towards the rear edge of cushion 10. In this general way a pumping action can be generated to help push blood through a user's legs (or any body portion of interest in contact with cushion 10) towards the heart and lungs. It can be noted from FIG. 4 that selective inflation/deflation can produce rearwardly advancing low pressure zones (the deflated cells). It can also be noted that typically no two deflated cells are adjacent at any one time. It is further noted that in some configurations, additional inflation states are contemplated for cells beyond the binary inflated and deflated states, such as ⅓ inflated, ½ inflated, ⅔ inflated, and the like, expanding options for configurations. The rear seat cushion edge is to the left in the FIG. 4 illustrations.

Figure 5:
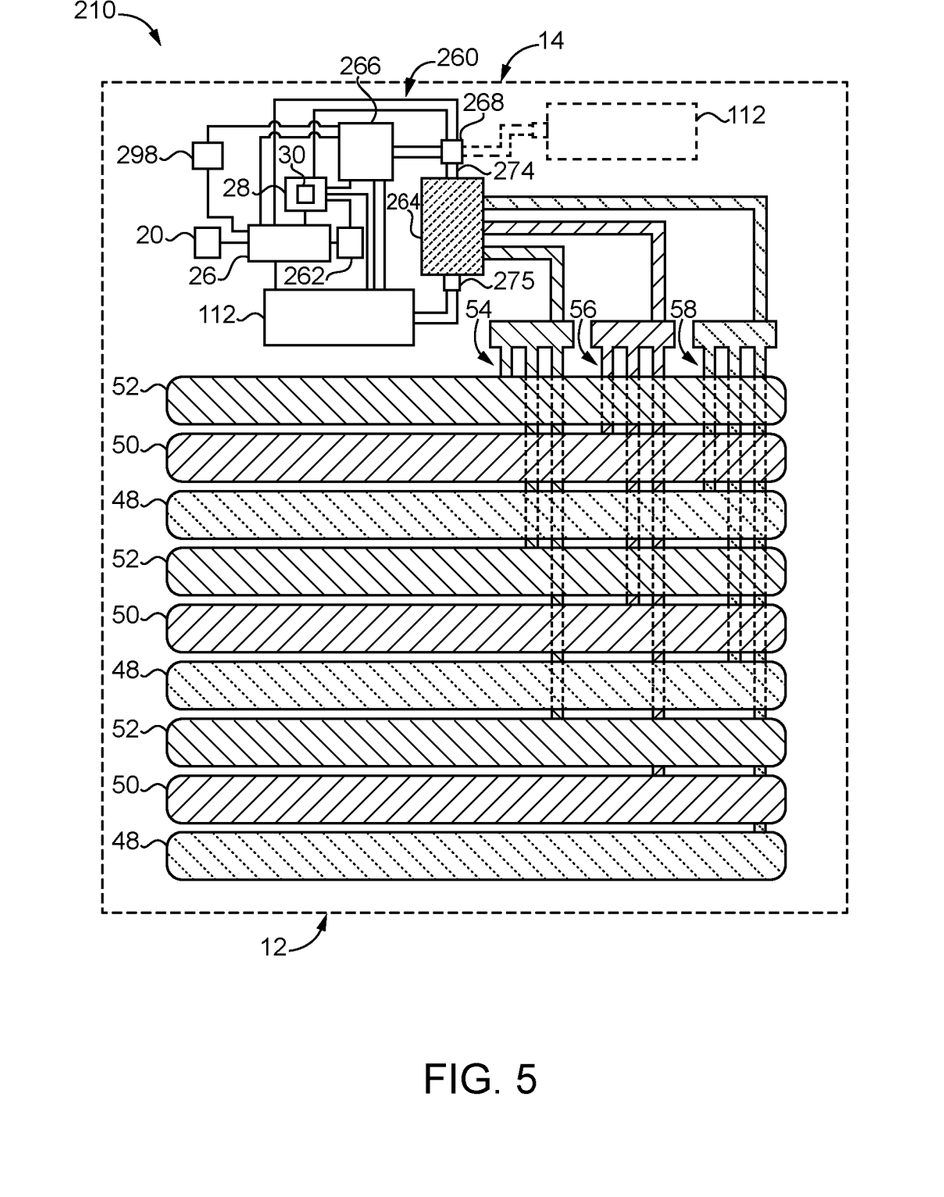
FIG. 5 is a schematic illustration of a cushion system, according to a second embodiment.

In some embodiments, a cushion according to the present disclosure, such as cushion 210 in FIG. 5, might include an air pressure monitoring system structured to monitor an air pressure parameter indicative of air pressure within one or more of inflatable cells 48, 50, 52, in conduits 54, 56, 58, or in another component of cushion 210. The air pressure monitoring system may include one or more sensors 298 communicatively coupled with electronic control unit 30 and positioned within or next to sitting surface 16. Sensor 298 can include any suitable pressure sensor, such as a capacitive, inductive, resistive, or other electronic sensor that changes its electrical or electromagnetic energy state in response to a change to, application of, or removal of, physical pressure upon a sensing element. Pressure sensor 298 could include an electrical switch having only an ON state and an OFF state in some embodiments. Electronic control unit 30 may be structured to receive data from the sensor(s) and determine, estimate, or infer the air pressure based on the received data. In other embodiments, electronic control unit 30 might be structured to determine air pressure by, for instance, measuring or determining a parameter of pumping mechanism 112, such as resistance to displacement of a pumping mechanism. The air pressure monitoring system could also detect a change in an air pressure parameter indicative of changing air pressure in one or more of inflatable cells 48, 50, 52 or analogous structures or components, and produce a signal in response. For instance, electronic control unit 30 may monitor a parameter indicative of air pressure to detect changes that might be indicative of a leak or a change in a patient's position on cushion 10, or that might indicate a patient stood up from or fell off cushion 10.

Electronic control unit 30 might also be structured to generate a signal responsive to a change in air pressure to cause pumping mechanism 112 to vary or discontinue a flow of air to inflatable cells 48, 50, 52, In other embodiments, the air pressure monitoring system might include an alarm, with electronic control unit 30 being structured to produce an alarm signal responsive to a change in air pressure or any other parameter. In still other embodiments, cushion 10 may include a wired or wireless transmitter, such as an RF, Bluetooth, or Wi-Fi transmitter coupled with circuitry 28. In such an embodiment, electronic control unit 30 may generate an alarm signal for the transmitter for transmission to a receiving device such as a mobile phone, a beeper (pager), a computer, or like device for the purpose of producing an alarm. In still other instances, the pressure parameter of interest might not necessarily be indicative of, or directly indicative of, air pressure in cushion 10, but instead include a sitting pressure of a user. For instance, pressure could be sensed in a part of cushion 10 whose pressure does not vary, or significantly vary, with inflation and deflation of the cells, but instead varies only based on the presence or absence of a person, or change in the applied weight of the person. Such an application could enable sensing the presence, absence, or body repositioning of a user in a manner analogous or complimentary to embodiments where air pressure is monitored. In still other instances, it is contemplated that sensed pressure feedback could be used for more sophisticated monitoring of patient positioning and behavior. In certain applications one or more pressure sensors can be positioned within cushion 10 and used to detect frequency and/or intensity of a user shifting his or her weight left, right, back, and the like. Logging such patterns of behavior over time is expected to elucidate trends that can be exploited or prevented in controlling and varying inflation and deflation of cushion 10 to optimize patient comfort and produce desired outcomes, such as prevention and/or treatment of pressure sores and the like. It is still further contemplated that pressure and body positioning/movement data gathered from a fleet of deployed cushions (garnered database) can enable optimized patterns of cushion inflation control to enable reduction in pressure sores and the like on a population level. Sensors 298 may be paired with the electronic controller 30 to vary treatment based on feedback. Sensors 298 may be paired with a ID code or signal unique to a particular patient to verify treatment received. In an institutional setting, it is contemplated that many cushions might be deployed to many different users, with a local communication system such as a Wi-Fi network or wired LAN, gathering data from the individual cushions as to use, efficacy, fall incidence, or other factors such as compliance with treatment regimens on a population level. It is also contemplated that cushions could be connected to a distribution system in a facility for pressurized air, or tanked air, with the cushions constructed without a resident pump at all. It is still further contemplated that treatment/use routines could be stored on a facility server, or a cloud server, and used to centrally control a fleet of cushions and/or receive and store usage data. Usage data herein could include adoption of treatment, in other words whether and/or the extent to which cushions are used, what specific patterns of inflation are adopted, or even confirmation that intended users are actually the ones using the cushions intended or controlled for their use. In an embodiment, a proximity sensor resident on a cushion could detect patient presence and/or patient identity by reading an electronically stored numerical patient identifier on a patient wristband or the like. This general concept could enable monitoring and potentially controlling dozens or even hundreds of devices in an effort to transform the health of a patient population or implement standardized treatment protocols. Each patient could have a user profile stored in a centralized database.

It will be appreciated that the valve arrangement illustrated in the attached drawings is exemplary only, and numerous alternative strategies might be successfully implemented. Analogously, while the zoned arrangement of the inflatable cells to provide a leading zone (red), a trailing zone (blue), and at least one middle zone (green) provides a practical implementation strategy, in other implementations more than three zones might be provided. It will further be appreciated that the presently disclosed strategy differs from other designs for therapeutic cushions where pressure was distributed between only two zones which, at best, provides only a back and forth motion (generating zero net fluid transport toward the heart and lungs) instead of a true pumping wave action a peristaltic pumping action). The present disclosure can be understood to enable producing a greater number of inflated cells that follow a lesser number of deflated cells, toward the rear seat cushion edge. The FIG. 3 illustration could be modified to show three inflated cells following two deflated cells, four inflated cells following three deflated cells, six inflated following one deflated, and so on with still other combinations. A plurality of pumping waves can be produced at any tune, with the number of waves typically being based on the number of repetitions in the serial, repeating arrangement of the leading, trailing, and at least one middle zone. Further still, embodiments are contemplated where an arrangement of separately controllable valves can vary the size and location of the different zones. For instance, valves could be selectively used to adjust the size of zones (size=number of cells) that are inflated and deflated to effectively vary the wavelength of the wave that is generated. Still other variations, such as those variations arising from varying the timing of the valve assembly actuation, contemplated herein relate to differences in amplitude and frequency of inflation and/or varying speed, amplitude, frequency, wavelength, and/or waveform (shape of the wave as determined by degree of inflation of cells) properties to tailor treatment parameters, and/or variations between the above-listed properties in a left series versus a right series of the inflatable cells such that a user's legs are treated differently from one another.

Referring still to FIG. 5 cushion 210 is similar to cushion 10 in many respects, but differs in that cushion 210 includes a unified valve system ("valve system") 260 for controlling a flow of air, or other inflation fluid, from pumping mechanism 112 to conduits 54, 56, 58 instead of individual valves (i.e., valves 36, 38, 40) for each conduit. Cushion 210, unlike the embodiment of cushion 10 shown in FIG. 3, also includes a wireless transmitter 262 coupled with circuitry 28 for wirelessly transmitting signals to a receiving device, such as a local server at a healthcare facility or a web server. It should be noted that like reference numerals are used to describe or denote like features across different embodiments without further explanation, it being understood that such features may be identical in construction and function to their counterparts discussed above. It should nevertheless be appreciated that no limitation is intended by way of the use of any particular reference numeral. Material differences between embodiments will be discussed herein. Absent such discussion, different embodiments should generally be understood to be alike in structure and function. Components described in connection with one embodiment may be included in other embodiments in which these components are not described or discussed. Unless expressly stated otherwise, components across embodiments having like features or functions can be understood as having like structures regardless of terminology.

Valve system 260 may include a valve assembly 264, a motor 266, and a clutch 268 coupling motor 266 with valve assembly 264. Valve assembly 264 is fluidly positioned between pumping mechanism 112 and conduits 54, 56, 58. Motor 266 might be a stepper motor coupled with battery 26 and circuitry 28, and structured to vary an angular position of a valve member 270 (as shown in FIGS. 6-10, discussed hereinafter) to selectively place pumping mechanism 112 in fluid communication with conduits 54, 56, 58. In other embodiments, valve system 260 might include a different type of motor or might include two or more motors. Motor 266 may also be structured to induce or cause a pumping action within pumping mechanism 112 such that air is pumped to valve assembly 264. Clutch 268 may be positioned between valve member 270 and motor 266 such that rotation of motor 266 can be selectively transferred to valve member 270 to vary its angular position while being able to also rotate to pumping mechanism 112 as needed. In some embodiments, pumping mechanism 112 might be coupled with clutch 268, as indicated by the dashed lines in FIG. 5, on a common output shaft or shaft assembly of motor 266. Thus, a single shaft or shaft assembly can extend from motor 266 to clutch 268 and to valve assembly 264. Rotating motor 266 in a first direction operates pumping mechanism 112, whereas rotating motor 266 in the opposite direction varies angular position of valve assembly 264, with clutch 268 serving as a torque transfer device that couples rotation of motor 266 in the first direction to pumping mechanism 112 but not valve assembly 264, and couples rotation of motor 266 in the second direction to valve assembly 264, and optionally but not necessarily to pumping mechanism 112. Clutch 268 could be engaged in the second direction to rotate valve assembly 264, but disengaged in the first direction. A variety of suitable mechanical clutches or electromechanical clutches could be used. A so-called freewheeling clutch provides one practical implementation strategy. Thus, rotation of motor 266 in the first direction operates pumping mechanism 112 without changing an angular position of valve assembly 264, and rotation of motor 266 in the second direction enables adjustment of valve assembly 264. Motor 266 can be digitally controlled such that when rotated to vary a position of valve assembly 264, valve member 270 can be positioned at relatively precise angular positions to obtain different valve/fluid flow configurations for filling or partially filling cells 48, 50, 52 and controlling cushion 10 as further discussed herein. Cushion 210 may include a sensor 298 communicatively coupled with circuitry 28, such as a pressure sensor structured to monitor a parameter of conduits 54, 56, 58, or of inflatable cells 48, 50, 52 indicative of air pressure therein. Sensor 298 might be a different type of sensor in other embodiments, such as a temperature sensor or a pressure sensor structure to detect a parameter indicative of force exerted upon cushion 210.

Figure 6:
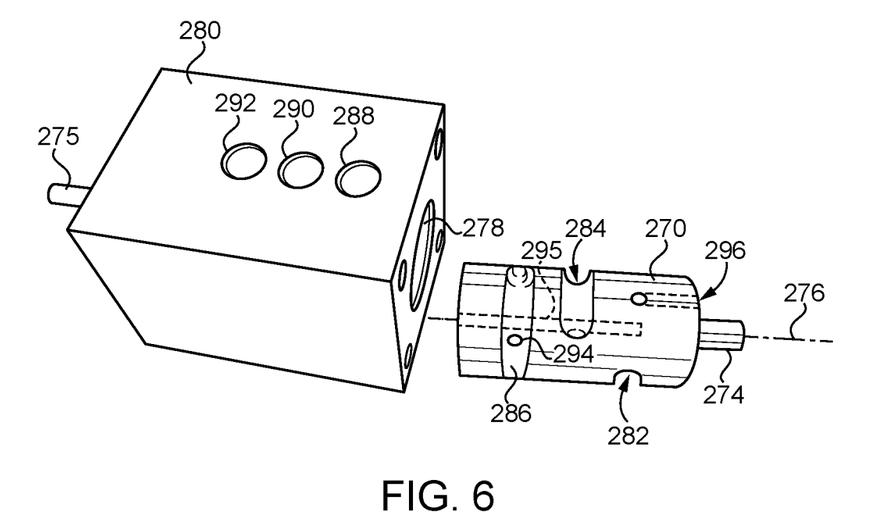
FIG. 6 is a perspective view of a valve assembly, according to one embodiment.
Figure 7:
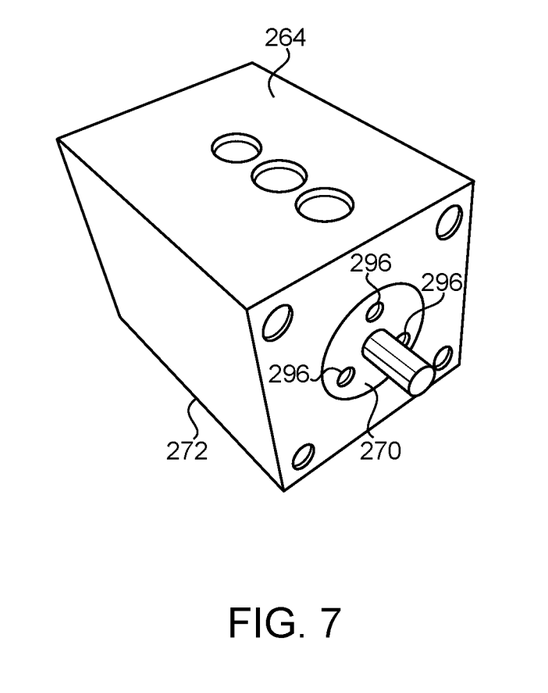
FIG. 7 is a perspective view of a valve assembly, according to one embodiment.

Referring now also to FIGS. 6 and 7, multiple perspective views of valve assembly 264 are shown. Valve assembly 264 includes valve member 270 rotatably positioned within a valve case 272. Valve member 270 may be generally cylindrical in shape with a protrusion or stub shaft 274 that defines an axis 276. Valve case 272 may have a cylindrical bore 278 structured to receive valve member 270, and includes a plurality of conduit bores extending between a surface 280 and cylindrical bore 278. Valve case 272 may also include an inlet fitting or the like 275 for fluidly coupling valve assembly 264 with pumping mechanism 112.

Valve member 270 includes a plurality of grooves each extending partially around valve member 270 in a circumferential direction. The number of moves formed in valve member 270 and the number of conduit bores formed in valve case 272 may correspond with the number of conduits within cushion 210, or with a number of inflation zones in cushion 210. By way of example, valve member 270 of the present embodiment includes a leading groove 282, a middle groove 284, and a trailing groove 286, and valve case 272 of the present embodiment includes a leading conduit bore 288, a middle conduit bore 290, and a trailing conduit bore 292. Leading groove 282 and leading conduit bore 288 correspond with inflatable cells 48, middle groove 284 and middle conduit bore 290 correspond with inflatable cells 50, and trailing groove 286 and trailing conduit bore 292 correspond with inflatable cells 52. In other embodiments, valve member 270 may include four or more grooves and a corresponding number of conduit bores. Grooves 282, 284, 286 may each extend approximately 270 degrees around valve member 270 and are axially and circumferentially offset from one another such that only two out of the three grooves are in fluid communication with the corresponding conduit bore at a time. In this way, varying an angular position of valve member 270 within cylindrical bore 278 can selectively place conduits 54, 56, 58 in fluid communication with pumping mechanism 112 to receive pressurized inflation fluid or connect to low pressure. In other embodiments, valve member 270 may have differently structured grooves. For instance, in an embodiment having more than three grooves, the grooves may have a lesser circumferential extent than grooves 282, 284, 286. Each groove may include a port 294 structured to permit fluid conveyed into a central valve member bore 295 from inlet fitting 275 to flow to the corresponding conduit bore 288, 290, 292. Valve member 270 may also include a plurality of outlet bores 296 extending therethrough to permit fluid to drain from inflatable cells 48, 50, 52. Outlet bores 286 each connect to a different outlet port formed in valve member 270 and circumferentially offset but axially aligned with a different one of grooves 282, 284, 286.

Figure 8:
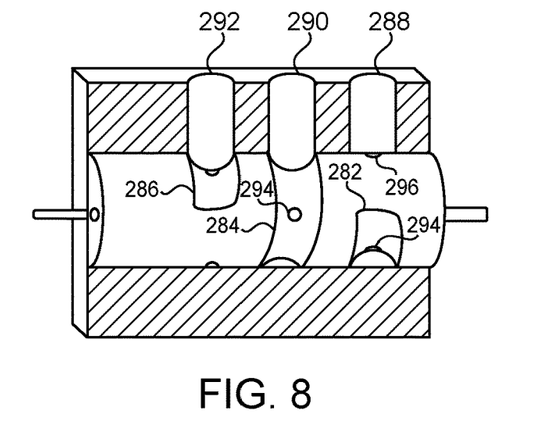
FIG. 8 is a partially sectioned view of a valve assembly, according to one embodiment.
Figure 9:
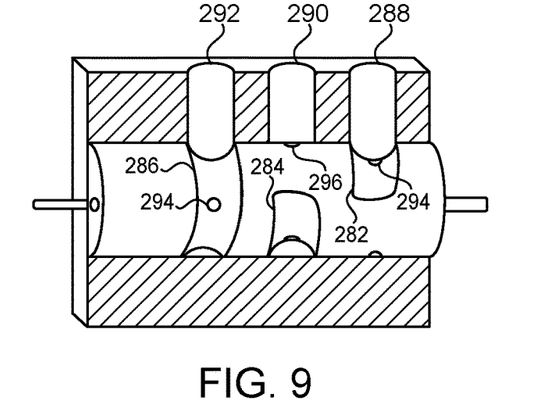
FIG. 9 is a partially sectioned view of a valve assembly, according to one embodiment.
Figure 10:
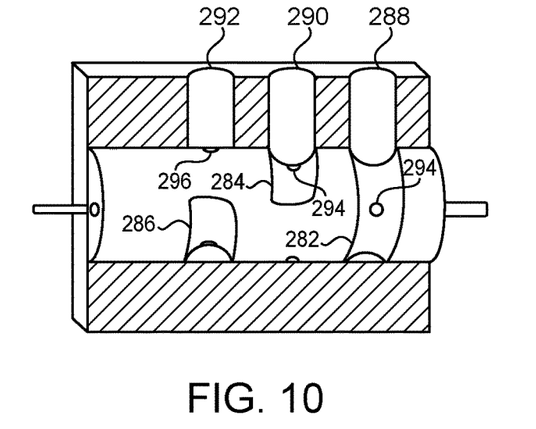
FIG. 10 is a partially sectioned view of a valve assembly, according to one embodiment.

Referring now also to FIGS. 8-10, partially sectioned views of valve assembly 264 are illustrated, showing valve member 270 at angular positions corresponding with initial configuration 55, second configuration 57, and third configuration 59, respectively. Motor 266 may be structured to rotate valve member 270 to one of the three angular positions. Each angular position may be digitally defined to correspond with a different inflation configuration of inflatable cells 48, 50, 52. For example, a first angular position (shown in FIG. 8) may correspond with initial configuration 55. Referring now also to FIG. 4, it can be seen that in initial configuration 55, inflatable cells 52, 50 are inflated and inflatable cells 48 are deflated or otherwise not fully inflated. To achieve this configuration, the first angular position may be digitally defined as a valve member position in which middle groove 284 is in fluid communication with middle conduit bore 290, trailing groove 286 is in fluid communication with trailing conduit bore 292, and leading conduit bore 288 is in fluid communication with outlet bore 296. Similarly, the second angular position (shown in FIG. 9) may correspond with second configuration 57, and the third angular position (shown in FIG. 10) may correspond with third configuration 59. Thus, valve system 260 may be capable of inducing a pumping wave/peristaltic pumping action by causing valve member 270 to rotate around axis 276 to defined or determined angular positions. In other embodiments, valve assembly 264 may be structured to selectively couple pumping mechanism 112 with conduits 54, 56, 58 through a different mechanism such as, for instance, by selectively energizing valves in a manner similar to that seen in FIG. 3.

The present description is for illustrative purposes only, and should not be construed to narrow the breadth of the present disclosure in any way. Thus, those skilled in the art will appreciate that nigh-infinite modifications might be made to the presently disclosed embodiments without departing from the full and fair scope and spirit of the present disclosure. For instance, while the present disclosure discusses electrical power and electronic control, the present disclosure is not limited in this regard. Embodiments are contemplated where an air supply, or other inflation fluid supply, drives fluid-based logic gates and/or timing circuits, and could therefore operate with fewer electrical components or potentially none at all. A control unit herein could be a fluid pressure control unit instead of electronic. Other aspects, features and advantages will be apparent upon an examination of the attached drawings and appended claims. As used herein, the articles "a" and "an" are intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A therapeutic cushion system comprising:
   a pumping mechanism;
   a seat cushion including at least three inflatable cells arranged in series between a front seat cushion edge and a rear seat cushion edge;
   the seat cushion further including a manifold having at least one inflation inlet in fluid communication with the pumping mechanism, and at least one deflation outlet;
   a valve assembly adjustable among at least three different valve configurations, and fluidly connecting some of the inflatable cells to the at least one inflation inlet and some of the inflatable cells to the at least one deflation outlet in each of the different valve configurations; and
   an electronic control unit structured to adjust the valve assembly among the at least three different valve configurations such that inflation/deflation of the inflatable cells produces a plurality of rearwardly advancing pumping waves;
   a fleet of cushions including the seat cushion;
   wherein the electronic control unit is configured to collect and record data associated with patient body positioning and movement for inclusion as part of a database garnered from the fleet of cushions for optimizing patient treatment.

2. The cushion system of claim 1 wherein the manifold includes fluid conduits connected to the inflatable cells in a zoned arrangement defining a leading zone, a trailing zone, and at least one middle zone.

3. The cushion system of claim 2 wherein the inflatable cells of the leading, trailing, and at least one middle zone, are in a serial, repeating arrangement between the front edge and the rear edge.

4. The cushion system of claim 3 wherein the electrically actuated valve assembly includes a first, a second, and a third valve mechanism positioned fluidly between inflatable cells of the leading, trailing, and at least one middle zone, respectively, and each of the at least one inflation inlet and the at least one deflation outlet.

5. The cushion system of claim 1 further comprising a cover having a cavity formed therein adjacent the rear edge and having the pumping mechanism positioned therein, and wherein:

the cushion is in a rolled-up configuration, and further comprising a tubular package retaining the cushion in the rolled-up configuration; and
the cover includes a plurality of regularly spaced grooves interspersed among the inflatable cells and defining fold lines along which the cover is folded in the rolled-up configuration.

6. The cushion system of claim 1 wherein the electronic control unit is further structured to produce the plurality of rearwardly advancing pumping waves by way of a plurality of low pressure zones.

7. The cushion system of claim 1 wherein the electronic control unit is structured to adjust electrical actuation of the valve assembly at variable speeds to define variable timing of the actuation of the valve assembly; and
   wherein varying the timing of the actuation of the valve assembly varies at least one property of the rearwardly advancing pumping waves selected from the group comprising speed, frequency, wavelength, amplitude, waveform, and combinations thereof.

8. The cushion system of claim 1 further including a pressure sensor communicatively coupled with the electronic control unit.

9. The cushion system of claim 1 further including a wireless transmitter communicatively coupled with the electronic control unit.

10. A cushion system comprising;
    a fluid source;
    an array of at least three inflatable cells defining a cushion and arranged in series between a front cushion edge and a rear cushion edge;
    a valve assembly including a valve member, at least one fluid inlet in fluid communication with the fluid source, and at least one fluid outlet;
    the valve assembly being adjustable among at least three different inflation configurations and fluidly connecting some of the inflatable cells to the at least one fluid inlet, and some of the inflatable cells to the at least one fluid outlet in each of the different inflation configurations; and
    an electronic control unit configured to adjust the valve assembly among the at least three different valve configurations such that a predetermined sequence of inflation and deflation of the respective inflatable cells produces a plurality of advancing pumping waves;
    a fleet of cushions including the seat cushion;
    wherein the electronic control unit is configured to collect and record data associated with patient body positioning and movement for inclusion as part of a database garnered from the fleet of cushions for optimizing patient treatment.

11. The cushion system of claim 10 wherein the electronic control unit is configured to vary actuation of the valve assembly to vary at least one property of the advancing pumping waves selected from the group comprising speed, frequency, wavelength, amplitude, waveform, and combinations thereof.

12. A cushion system comprising;
    an array of inflatable cells defining a cushion and arranged in series between a front cushion edge and a rear cushion edge;
    fluid conduits connecting to the inflatable cells in a zoned arrangement defining a first zone, a second zone, and a third zone, of the inflatable cells; and
    an electrically actuated valve assembly including at least one fluid inlet, at least one fluid outlet, and at least one valve member positioned fluidly between the at least one fluid outlet and each of the respective first, second, and third zones, and the valve assembly is adjustable by moving the valve member among a plurality of inflation configurations;

in a first of the plurality of inflation configurations the first zone is fluidly connected for deflation to the at least one fluid outlet, and each of the second zone and the third zone is not fluidly connected to the at least one fluid outlet;

in a second of the plurality of inflation configurations the second zone is fluidly connected for deflation to the at least one fluid outlet and the first zone and third zone are not fluidly connected to the at least one fluid outlet; and in a third of the plurality of inflation configurations the third zone is fluidly connected to the at least one fluid outlet, and the first zone and the second zone are not fluidly connected to the at least one fluid outlet;

a fleet of cushions including the seat cushion;

wherein the electronic control unit is configured to collect and record data associated with patient body positioning and movement for inclusion as part of a database garnered from the fleet of cushions for optimizing patient treatment.

13. The cushion system of claim 12 wherein each of the respective first, second, and third zones includes a plurality of the inflatable cells.

14. The cushion system of claim 12 wherein the first zone includes a leading zone, the second zone includes a trailing zone, and the third zone includes a middle zone.

15. The cushion system of claim 14 further comprising an electronic control unit configured to adjust the valve assembly among the plurality of different valve configurations in a sequence of inflation and deflation producing advancing pumping waves.

16. The cushion system of claim 14 wherein in each of the plurality of different valve configurations a greater number of the inflatable cells is inflated and a lesser number of the inflatable cells is deflated.

17. The cushion system of claim 14 wherein the sequence of advancing pumping waves produces a peristaltic pumping action.

18. The cushion system of claim 14 wherein an electronic control unit is further configured to vary the adjustment of the valve assembly to vary at least one of a speed, a frequency, a wavelength, an amplitude, or waveform, of the advancing pumping waves.

* * * * *